United States Patent
Itoh et al.

(10) Patent No.: US 10,533,073 B2
(45) Date of Patent: Jan. 14, 2020

(54) 2-CYANOETHYL-CONTAINING ORGANOXYSILANE COMPOUND, SILSESQUIOXANE, AND MAKING METHODS

(71) Applicant: SHIN-ETSU CHEMICAL CO., LTD., Tokyo (JP)

(72) Inventors: Yusuke Itoh, Joetsu (JP); Ayumu Kiyomori, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/695,702

(22) Filed: Sep. 5, 2017

(65) Prior Publication Data
US 2018/0066112 A1    Mar. 8, 2018

(30) Foreign Application Priority Data

Sep. 6, 2016 (JP) .................. 2016-173335

(51) Int. Cl.
*C08G 77/04* (2006.01)
*C08G 77/08* (2006.01)
(Continued)

(52) U.S. Cl.
CPC ........... *C08G 77/045* (2013.01); *C08G 77/08* (2013.01); *C08G 77/18* (2013.01); *C08G 77/20* (2013.01); *C08G 77/38* (2013.01); *C08J 3/246* (2013.01)

(58) Field of Classification Search
CPC ........ C07F 7/0838; C07F 7/1804; C07F 7/21; C08G 77/045; C08G 77/08; C08G 77/18; C08G 77/20; C08G 77/38; C08J 3/246
See application file for complete search history.

(56) References Cited

U.S. PATENT DOCUMENTS 3,033,815 A * 5/1962 Pike .................. C02F 1/545
                                               528/25
8,461,368 B2   6/2013 Kim et al.
(Continued)

FOREIGN PATENT DOCUMENTS

EP    1717240 A1   11/2006
GB     882051 A    11/1961
(Continued)

OTHER PUBLICATIONS

Sultanov, R. et al. "Synthesis of unsaturated silicon-containing amines" Azerbaidzhanskii Khimicheskii Zhurnal, Issue: 2, pp. 97-102, Journal, 1964; Abstract only (Year: 1964).*

(Continued)

*Primary Examiner* — Medhanit W Bahta
(74) *Attorney, Agent, or Firm* — Birch, Stewart, Kolasch & Birch, LLP (57) ABSTRACT

A 2-cyanoethyl-containing organoxysilane compound having the formula: $NC-CH_2-CH_2-X-Si(OR^1)_3$ is heat resistant and compatible with organic solvents. $R^1$ is a $C_1$-$C_{20}$ monovalent hydrocarbon group, and X is a $C_2$-$C_{20}$ divalent hydrocarbon group which contains a methylene and/or methine moiety, at least one of the methylene and methine moieties being substituted with a divalent heteroatom linking moiety NR (wherein R is hydrogen, $C_1$-$C_{20}$ monovalent hydrocarbon group or 2-cyanoethyl), a trivalent heteroatom linking moiety N, or a combination thereof.

2 Claims, 3 Drawing Sheets

(51) Int. Cl.
*C08G 77/18* (2006.01)
*C08G 77/20* (2006.01)
*C08G 77/38* (2006.01)
*C08J 3/24* (2006.01)

(56) References Cited

U.S. PATENT DOCUMENTS

2009/0075096 A1 3/2009 Butikofer et al.
2012/0142793 A1 6/2012 Frey et al.

FOREIGN PATENT DOCUMENTS

| JP | 2009-059651 A | 3/2009 |
| JP | 2010-511695 A | 4/2010 |

OTHER PUBLICATIONS

Database WPI Week 200722, "Silicomethane Coupling Agent Containing Cyanide and Secondary Amino and its Preparation Process and Application Thereof," Thompson Scientific, London, GB; AN 2007-207917, XP002775660, Jun. 28, 2006, 1 page.
Extended European Search Report for European Application No. 17188686.4, dated Dec. 8, 2017.
Xu et al., "Influence of Incorporating $CaCO_3$ into Room Temperature Vulcanized Silicone Sealant on Its Mechanical and Dynamic Rheological Properties," Journal of Applied Polymer Science, vol. 103, 2007, pp. 2027-2035.
Chen et al., "Preparation of silica gel supported amidoxime adsorbents for selective adsorption of Hg(II) from aqueous solution", Chemical Engineering Journal, 2012, vol. 209, pp. 235-244.
Sultanov et al., "Synthesis of Silicon-Containing Epoxyaminopropionitriles", Zhurnal Obshchei Khimii, Mar. 1967, vol. 37, No. 3, pp. 739-741.

* cited by examiner

2-CYANOETHYL-CONTAINING ORGANOXYSILANE COMPOUND, SILSESQUIOXANE, AND MAKING METHODS

CROSS-REFERENCE TO RELATED APPLICATION

This non-provisional application claims priority under 35 U.S.C. § 119(a) on Patent Application No. 2016-173335 filed in Japan on Sep. 6, 2016, the entire contents of which are hereby incorporated by reference.

TECHNICAL FIELD

This invention relates to 2-cyanoethyl-containing organoxysilane compounds, silsesquioxanes, and methods for preparing the same.

BACKGROUND ART

Cyano-containing organoxysilane compounds are generally used as silane coupling agents and HPLC column treating agents. They are also useful in organic-inorganic hybrid materials because the cyano group can be converted to carboxylic acid or amide via hydrolysis and to amine or aldehyde via reductive reaction.

Among known cyano-containing organoxysilane compounds, for example, Non-Patent Document 1 describes γ-aminopropylmethyldiethoxysilane having two molecules of acrylonitrile added thereto. Non-Patent Document 2 describes epoxyaminopropionitrile having a hydrolyzable silyl group. Patent Document 1 discloses cyano-containing organoxysilane compounds having an ester moiety.

In general, organoxysilane compounds are hydrolyzed into polysiloxanes which are ready for use. In particular, a three-dimensional network polysiloxane of $(RSiO_{3/2})_n$ structure obtained from hydrolysis of a trifunctional silane is known as "silsesquioxane." The silsesquioxane has thermal, dynamic and chemical stability and may be given various properties by introducing a functional group.

As a typical silsesquioxane having a cyano group, Patent Document 2 discloses a silsesquioxane obtained from co-hydrolysis of cyanoethyltriethoxysilane and methyltrimethoxysilane, which is useful as gate dielectrics for organic TFTs. The cyano group contributes to an improvement in dielectric constant.

CITATION LIST

Patent Document: 1: JP-A 2010-511695
Patent Document: 2: JP-A 2009-059651
Non-Patent Document 1: Chemical Engineering Journal, 209, 235-244, 2012
Non-Patent Document 2: Zhurnal Obshchei Khimii, 37, 3, 739-41, 1967

SUMMARY OF INVENTION

The foregoing organoxysilane compounds, however, have drawbacks. The organoxysilane compounds having a β-cyanoester structure described in Patent Document 1 are quite susceptible to hydrolysis or transesterification because of high reactivity of the ester moiety. In some cases, the desired silsesquioxane is not obtainable.

The silsesquioxane containing a 2-cyanoethyl group described in Patent Document 2 is available in solution form. When the silsesquioxane is isolated in order to remove the residual silanol, it often loses compatibility with organic solvents.

On hydrolysis, the difunctional organoxysilane compounds of Non-Patent Document 1 form linear or cyclic siloxane compounds, which have poor heat resistance as compared with the silsesquioxanes obtained from hydrolysis of trifunctional organoxysilane compounds.

On hydrolysis of the epoxy-containing organoxysilane compounds of Non-Patent Document 2, a hydroxyl group resulting from the epoxy group undergoes intramolecular reaction with trialkoxysilane. This results in more crosslinking points, sometimes inviting a lowering of compatibility with organic solvents.

An object of the invention is to provide a 2-cyanoethyl-containing silsesquioxane having heat resistance and compatibility with organic solvents, and a 2-cyanoethyl-containing organoxysilane compound as a starting reactant therefore.

The inventors have found that a silsesquioxane is obtained from hydrolysis of a 2-cyanoethyl-containing organoxysilane compound, and the resulting silsesquioxane has improved heat resistance and compatibility with organic solvents.

In one aspect, the invention provides a 2-cyanoethyl-containing organoxysilane compound having the general formula (1).

$$NC-CH_2-CH_2-X-Si(OR^1)_3 \qquad (1)$$

Herein $R^1$ is each independently a $C_1$-$C_{20}$ straight, branched or cyclic monovalent hydrocarbon group, and X is a $C_2$-$C_{20}$ straight, branched or cyclic divalent hydrocarbon group which contains a methylene and/or methine moiety, at least one of the methylene and methine moieties being substituted by a divalent heteroatom linking moiety NR wherein R is hydrogen, $C_1$-$C_{20}$ monovalent hydrocarbon group or 2-cyanoethyl, a trivalent heteroatom linking moiety N, or a combination thereof, with the proviso that the heteroatom linking moieties do not adjoin each other, the heteroatom linking moiety does not adjoin a silicon atom, and the $NC-CH_2CH_2-$ linkage is bonded to the heteroatom linking moiety included in X.

Preferably, R is a $C_1$-$C_6$ straight monovalent hydrocarbon group or 2-cyanoethyl.

In a second aspect, the invention provides a method for preparing the 2-cyanoethyl-containing organoxysilane compound of formula (1), comprising the step of Michael addition reaction of an organoxysilane compound having the general formula (2) with acrylonitrile, $$HX-Si(OR^1)_3 \qquad (2)$$

wherein $R^1$ and X are as defined above, and the hydrogen atom H in the formula is bonded to the heteroatom linking moiety included in X.

In a third aspect, the invention provides a silsesquioxane having the general formula (3).

$$[NCH_2CH_2C-X-SiO_{3/2}]_p[Z-SiO_{3/2}]_q \qquad (3)$$

Herein X is a $C_2$-$C_{20}$ straight, branched or cyclic divalent hydrocarbon group which contains a methylene and/or methine moiety, at least one of the methylene and methine moieties being substituted by a divalent heteroatom linking moiety NR wherein R is hydrogen, $C_1$-$C_{20}$ monovalent hydrocarbon group or 2-cyanoethyl, a trivalent heteroatom linking moiety N, or a combination thereof, with the proviso that the heteroatom linking moieties do not adjoin each other, the heteroatom linking moiety does not adjoin a silicon atom, and the NC—CH$_2$—CH$_2$— linkage is bonded to the heteroatom linking moiety included in X. Z is a substituted or unsubstituted, C$_1$-C$_{20}$ straight, branched or cyclic monovalent hydrocarbon group, p is an integer of 1 to 150, q is an integer of 0 to 100, and p+q is 4 to 150.

In a fourth aspect, the invention provides a method for preparing a silsesquioxane having the general formula (3):

[NCH$_2$CH$_2$C—X—SiO$_{3/2}$]$_p$[Z—SiO$_{3/2}$]$_q$     (3)

wherein X is as defined above, Z is a substituted or unsubstituted, C$_1$-C$_{20}$ straight, branched or cyclic monovalent hydrocarbon group, p is an integer of 4 to 150, and q is 0, the method comprising the step of effecting hydrolysis and condensation of the 2-cyanoethyl-containing organoxysilane compound of formula (1).

In a fifth aspect, the invention provides a method for preparing a silsesquioxane having the general formula (3):

[NCH$_2$CH$_2$C—X—SiO$_{3/2}$]$_p$[Z—SiO$_{3/2}$]$_q$     (3)

wherein X and Z are as defined above, p is an integer of 1 to 150, q is an integer of 1 to 100, and p+q is 4 to 150, the method comprising the step of effecting co-hydrolysis and condensation of the 2-cyanoethyl-containing organoxysilane compound of formula (1) with at least one trifunctional organoxysilane compound having the general formula (4):

Z—SiR$^2_3$     (4)

wherein R$^2$ is a group which becomes hydrolytic upon bonding with a silicon atom, Z is a substituted or unsubstituted, C$_1$-C$_{20}$ straight, branched or cyclic monovalent hydrocarbon group.

Preferably, R$^2$ is a C$_1$-C$_6$ organoxy group, C$_1$-C$_3$ acyloxy group or halogen atom.

Advantageous Effects of Invention

The silsesquioxane obtained from hydrolysis of a 2-cyanoethyl-containing silane compound of specific structure has improved heat resistance and compatibility with organic solvents. The 2-cyanoethyl group contributes to an improvement in dielectric constant. Because of these advantageous properties, the silsesquioxane is useful in ink compositions, LED encapsulating compositions, and gate dielectrics for organic TFTs.

DESCRIPTION OF PREFERRED EMBODIMENTS

2-Cyanoethyl-Containing Organoxysilane Compound

One embodiment of the invention is a 2-cyanoethyl-containing organoxysilane compound having the general formula (1).

NC—CH$_2$—CH$_2$—X—Si(OR$^1$)$_3$     (1)

In formula (1), the CN group is a highly polar substituent. When the organoxysilane compound having formula (1) is converted into a silsesquioxane through hydrolytic reaction, the CN group imparts a functionality such as an improvement in dielectric constant to the silsesquioxane.

R$^1$ is a C$_1$-C$_{20}$, preferably C$_1$-C$_{10}$, more preferably C$_1$-C$_6$ straight, branched or cyclic monovalent hydrocarbon group. Examples of the monovalent hydrocarbon group include straight alkyl groups such as methyl, ethyl, n-propyl, n-butyl, n-hexyl, n-heptyl, n-octyl, n-nonyl, and n-decyl; branched alkyl groups such as isopropyl, isobutyl, sec-butyl, tert-butyl, isopentyl, 2-pentyl, 3-pentyl, and tert-pentyl; cyclic alkyl groups such as cyclopropyl, cyclohexyl, cyclopentyl, and cyclooctyl; and unsaturated hydrocarbon groups including alkenyl groups such as vinyl, allyl, 1-propenyl, 1-methylpropenyl, butenyl, pentenyl, hexenyl, heptenyl, octenyl, nonenyl, decenyl, undecenyl, and octadecenyl, and alkynyl groups such as ethynyl and propynyl; aryl groups such as phenyl, tolyl, xylyl, mesityl, naphthyl, and biphenyl; and aralkyl groups such as benzyl, phenethyl, phenylpropyl and phenylbutyl.

X is a C$_2$-C$_{20}$ straight, branched or cyclic divalent hydrocarbon group which contains a methylene and/or methine moiety. At least one of the methylene and methine moieties is substituted with a divalent heteroatom linking moiety NR (wherein R is defined below), a trivalent heteroatom linking moiety N, or a combination thereof, with the proviso that the heteroatom linking moieties do not adjoin each other, the heteroatom linking moiety does not adjoin a silicon atom, and the NC—CH$_2$—CH$_2$— linkage is bonded to the heteroatom linking moiety included in X. The inclusion of N atom contributes to an improvement n the compatibility of the organoxysilane with organic solvents.

Examples of the divalent hydrocarbon group constituting the framework of X include straight aliphatic alkanediyl groups such as ethanediyl, propanediyl, butanediyl, pentanediyl, hexanediyl, heptanediyl, octanediyl, nonanediyl, decanediyl, undecanediyl, dodecanediyl, tridecanediyl, tetradecanediyl, pentadecanediyl, hexadecanediyl, heptadecanediyl, octadecanediyl, and nonadecanediyl; branched aliphatic alkanediyl groups such as 2-methylpropanediyl, 2-ethylpropanediyl, 4-methylheptanediyl, 4-ethylheptanediyl, 4-propylheptanediyl, 2-butylheptanediyl, 3-propyloctanediyl, 2-butylnonanediyl, 4-methyldecanediyl, 4-ethyldecanediyl, 3-propyldecanediyl, 2-butyldecanediyl, and 3-butylundecanediyl; and cycloaliphatic alkanediyl groups such as cyclohexanediyl, ethylcyclohexanediyl, propylcyclohexanediyl, 4-ethyl-1-methyl-2-propylcyclohexanediyl, and 4-ethyl-2-methyl-1-propylcyclohexanediyl. From the standpoint of ease of distillation purification, preference is given to C$_2$-C$_6$ divalent straight aliphatic hydrocarbon groups, C$_3$-C$_6$ divalent branched aliphatic hydrocarbon groups, and C$_7$-C$_{12}$ divalent cycloaliphatic hydrocarbon groups.

As mentioned above, in the divalent hydrocarbon group constituting the framework of X, at least one, preferably one to four, more preferably one or two of the methylene and methine moieties is substituted by a divalent heteroatom linking moiety NR, a trivalent heteroatom linking moiety N, or a combination thereof.

In the heteroatom linking moiety NR, R is hydrogen, a C$_1$-C$_{20}$ monovalent hydrocarbon group or 2-cyanoethyl group. The C$_1$-C$_{20}$ monovalent hydrocarbon groups may be straight, branched or cyclic. Examples include C$_1$-C$_{20}$, preferably C$_1$-C$_{10}$, more preferably C$_1$-C$_6$ straight alkyl groups such as methyl, ethyl, n-propyl, n-butyl, n-pentyl, n-hexyl, n-heptyl, n-octyl, n-nonyl, and n-decyl; C$_3$-C$_{20}$, preferably

$C_3$-$C_{10}$, more preferably $C_3$-$C_6$ branched alkyl groups such as isopropyl, isobutyl, sec-butyl, tert-butyl, isopentyl, 2-pentyl, 3-pentyl, and tert-pentyl; cyclic alkyl groups such as cyclopropyl, cyclobutyl, cyclohexyl, cyclopentyl, and cyclooctyl; $C_6$-$C_{12}$ aryl groups such as phenyl, tolyl, xylyl, mesityl, naphthyl, and biphenyl; and $C_7$-$C_{10}$ aralkyl groups such as benzyl, phenethyl, phenylpropyl and phenylbutyl. From the standpoint of ease of distillation purification, preference is given to $C_1$-$C_5$ straight alkyl groups, $C_3$-$C_6$ branched alkyl groups, and $C_3$-$C_6$ cyclic alkyl groups.

Examples of X include 1-(2-cyanoethyl)-1-aza-1,4-butanediyl, 1-(3-cyanopropyl)-1-aza-1,4-butanediyl, 1-methyl-1-aza-1,4-butanediyl, 1-ethyl-1-aza-1,4-butanediyl, 1-propyl-1-aza-1,4-butanediyl, 1-butyl-1-aza-1,4-butanediyl, 1-pentyl-1-aza-1,4-butanediyl, 1-hexyl-1-aza-1,4-butanediyl, 1,4-bis(2-cyanoethyl)-1,4-diaza-1,6-hexanediyl, 1-phenyl-1-aza-1,4-butanediyl, 1-isopropyl-1-aza-1,4-butanediyl, and 1,4-piperadino-1,7-heptanediyl.

Examples of the compound having formula (1) are given below, but not limited thereto.

(1-1)

(1-2)

(1-3)

(1-4)

(1-5)

(1-6)

(1-7)

(1-8)

(1-9)

(1-10)

(1-11)

(1-12)

(1-13)

(1-14)

(1-15)

(1-16)

The 2-cyanoethyl-containing organoxysilane compound having formula (1) is prepared by effecting Michael addition reaction of an organoxysilane compound having the general formula (2) with acrylonitrile.

(2)

(1)

Herein R¹ and X are as defined above, and the hydrogen atom H in the formula is bonded to the heteroatom linking moiety included in X.

The organoxysilane compound having formula (2) may be combined with acrylonitrile in any desired ratio. Preferably 1 to 4 moles, more preferably 1 to 3 moles, and even more preferably 1 to 2.2 moles of acrylonitrile is used per mole of the organoxysilane compound having formula (2).

In the preparation method, a catalyst may be added for the purpose of promoting the reaction. Suitable catalysts include sulfonic acids such as trifluoromethanesulfonic acid, dodecylbenzenesulfonic acid, methanesulfonic acid, p-toluenesulfonic acid, 1,1,2,2-tetrafluoroethanesulfonic acid and 1,1,2,2,2-pentafluoroethanesulfonic acid; carboxylic acids such as formic acid, acetic acid, propionic acid, citric acid, succinic acid, and benzoic acid; metal hydroxides such as potassium hydroxide, sodium hydroxide and cesium hydroxide; alkali metal alkoxides such as potassium methoxide, sodium methoxide, potassium tert-butoxide, sodium tert-butoxide, and sodium ethoxide; and inorganic bases such as ammonium carbonate, sodium carbonate, potassium carbonate, ammonium hydrogencarbonate, sodium hydrogencarbonate, and potassium hydrogencarbonate. Inter alia, sulfonic acids and metal hydroxides are preferred.

The amount of the catalyst used is not particularly limited. From the standpoints of reactivity and productivity, it is preferred to use 0.0001 to 0.5 mole, more preferably 0.001 to 0.3 mole, and even more preferably 0.01 to 0.1 mole of the catalyst per mole of the compound having formula (2).

Although the reaction temperature is not particularly limited, it is preferably 0 to 200° C., more preferably 30 to 150° C., and even more preferably 50 to 130° C. Although the reaction time is not particularly limited, it is preferably 1 to 60 hours, more preferably 1 to 30 hours, and even more preferably 1 to 20 hours. The reaction atmosphere is preferably an inert gas atmosphere such as nitrogen or argon although air is acceptable.

Although the reaction takes place in a solventless system, a solvent may be used. Suitable solvents include hydrocarbon solvents such as pentane, hexane, cyclohexane, heptane, isooctane, toluene, and xylene, alcohol solvents such as methanol, ethanol, 1-propanol, 2-propanol, 1-butanol, and 2-butanol, and aprotic polar solvents such as acetonitrile, N,N-dimethylformamide, and N-methylpyrrolidone, which may be used alone or in admixture. Inter alia, alcohol solvents are preferred because they are also effective for promoting the reaction.

At the end of reaction, the catalyst, if used, is preferably neutralized. If the reaction solution is purified by distillation without neutralization, reverse Michael reaction can take place during distillation, resulting in lower yields. For neutralization, an acid or base may be used, which is selected from those exemplified as the catalyst. Although the amount of the neutralizing agent is not particularly limited, the amount may be 1.0 to 2.0 moles, preferably 1.0 to 1.8 moles, and more preferably 1.0 to 1.5 moles per mole of the catalyst. If the neutralizing agent is used in excess, it may be back neutralized by further adding an acid or base. For back-neutralization, any compound as exemplified for the catalyst may be used. The amount of the back-neutralizing agent is preferably 1.0 to 2.0 moles, more preferably 1.0 to 1.5 moles per mole of the excess of neutralizing agent.

The 2-cyanoethyl-containing organoxysilane compound obtained by the above-mentioned method may be purified by any suitable means such as distillation, filtration, washing, column separation, or solid adsorbent, depending on the desired quality, prior to use. Distillation purification is preferably used to remove trace impurities such as catalyst whereby the compound of high purity is obtainable.

Silsesquioxane

Another embodiment of the invention is a silsesquioxane having the general formula (3).

$$[NCH_2CH_2C-X-SiO_{3/2}]_p[Z-SiO_{3/2}]_q \quad (3)$$

In formula (3), X is as defined above, and Z is a substituted or unsubstituted, $C_1$-$C_{20}$, preferably $C_1$-$C_{10}$, more preferably $C_1$-$C_6$ straight, branched or cyclic monovalent hydrocarbon group.

The monovalent hydrocarbon group Z is as defined and exemplified in conjunction with formula (1). Examples of Z include straight alkyl groups such as methyl, ethyl, n-propyl, n-butyl, n-pentyl, n-hexyl, n-heptyl, n-octyl, n-nonyl, and n-decyl; branched alkyl groups such as isopropyl, isobutyl, sec-butyl, tert-butyl, isopentyl, 2-pentyl, 3-pentyl, and tert-pentyl; cyclic alkyl groups such as cyclopropyl, cyclohexyl, cyclopentyl, and cyclooctyl; and unsaturated hydrocarbon groups including alkenyl groups such as vinyl, allyl, 1-propenyl, 1-methylpropenyl, butenyl, pentenyl, hexenyl, heptenyl, octenyl, nonenyl, decenyl, undecenyl, and octadecenyl, and alkynyl groups such as ethynyl and propynyl; aryl groups such as phenyl, tolyl, xylyl, mesityl, naphthyl, and biphenyl; and aralkyl groups such as benzyl, phenethyl, phenylpropyl and phenylbutyl.

One or more or even all hydrogen atoms on the hydrocarbon group may be substituted. Suitable substituents include alkoxy groups such as methoxy, ethoxy, and propoxy, halogen atoms such as fluorine, chlorine, bromine and iodine, cyano groups, and amino groups.

The subscript p is an integer of 1 to 150, preferably 4 to 100, more preferably 6 to 100, and even more preferably 6 to 50. If p is less than 1, the compound having formula (3) has a low molecular weight and insufficient heat resistance. If p exceeds 150, the compound having formula (3) is less compatible with organic solvents.

The subscript q is an integer of 0 to 100, and p+q is an integer of 4 to 150, preferably 4 to 100, more preferably 6 to 50, and even more preferably 6 to 30. If p+q is less than 4, the compound having formula (3) has a low molecular weight and insufficient heat resistance. If p+q exceeds 150, the compound having formula (3) is less compatible with organic solvents.

In view of compatibility with organic solvents, the silsesquioxane having formula (3) should preferably have a number average molecular weight (Mn) of 300 to 50,000, more preferably 400 to 40,000, and even more preferably 500 to 30,000, as measured versus polystyrene standards by gel permeation chromatography (GPC).

The silsesquioxane having formula (3) may be prepared as follows.

i) q=0

The silsesquioxane having formula (3) may be prepared by hydrolysis and condensation of a 2-cyanoethyl-containing organoxysilane compound having formula (1). Hydrolysis and condensation of the organoxysilane compound having formula (1) may be performed in a well-known way. For example, the 2-cyanoethyl-containing organoxysilane compound is reacted with water in a solvent. Suitable solvents include hydrocarbon solvents such as hexane, heptane, octane, isooctane, decane, toluene, xylene, and mesitylene, alcohol solvents such as methanol, ethanol, propanol, 2-propanol, butanol, 2-butanol, and tert-butanol, nitrile solvents such as acetonitrile, propionitrile, and benzonitrile, amide solvents such as dimethylformamide, dimethylacetamide and N-methylpyrrolidone, and ether solvents such as diethyl ether, tetrahydrofuran, cyclopentyl methyl ether and 1,2-dimethoxyethane.

The hydrolysis and condensation may be accelerated by adding an acid or base as a catalyst or by heating. Examples of the acid used as catalyst include carboxylic acids such as formic acid, acetic acid, propionic acid, citric acid, and benzoic acid; sulfonic acids such as methanesulfonic acid, toluenesulfonic acid, and dodecylbenzenesulfonic acid; and mineral acids such as hydrochloric acid, sulfuric acid, nitric acid and phosphoric acid. Examples of the base include ammonia and organic amines such as ethyldimethylamine, diethylmethylamine, triethylamine, tributylamine, and diisopropylethylamine; and inorganic bases such as sodium hydroxide, potassium hydroxide, cesium hydroxide, ammonium carbonate, sodium carbonate, potassium carbonate, ammonium hydrogencarbonate, sodium hydrogencarbonate, and potassium hydrogencarbonate.

ii) q≠0 (i.e., q is an Integer of 1 to 100)

The silsesquioxane having formula (3) may be prepared by co-hydrolysis and condensation of a 2-cyanoethyl-containing organoxysilane compound having formula (1) and at least one trifunctional organoxysilane compound having the general formula (4).

$$Z—SiR^2{}_3 \quad (4)$$

In formula (4), $R^2$ is a group which becomes hydrolytic upon bonding with a silicon atom, and Z is as defined above. Examples of the group which becomes hydrolytic upon bonding with a silicon atom, represented by $R^2$, include $C_1$-$C_6$ organoxy groups, $C_1$-$C_3$ acyloxy groups, and halogen atoms. Suitable $C_1$-$C_6$ organoxy groups include alkoxy groups such as methoxy, ethoxy, n-propoxy, n-butoxy, n-pentyloxy, n-hexyloxy, isopropoxy, isobutoxy, sec-butoxy, tert-butoxy, isopentyloxy, 2-pentyloxy, cyclopentyloxy, and cyclohexyloxy; alkenoxy groups such as vinyloxy and 2-propenoxy; and phenoxy. Suitable $C_1$-$C_3$ acyloxy groups include acetoxy, ethanoyloxy and propanoyloxy. Suitable halogen atoms include chlorine, bromine and iodine.

Also hydrolysis and condensation of a 2-cyanoethyl-containing organoxysilane compound having formula (1) may be carried out in the co-presence of a trifunctional organoxysilane compound having formula (4) by the same method as the reaction of the organoxysilane of formula (1) alone.

In the silsesquioxane having formula (3), there may remain a substituent $OR^1$ which has not been hydrolyzed or a substituent OH which has been hydrolyzed, but not condensed. In such silsesquioxane having formula (3), it is preferred in view of the stability of the green or cured composition that the proportion of silicon atoms bonded to the substituent $OR^1$ or OH be 0 to 25 mol %, more preferably 0 to 15 mol % of the overall silicon atoms.

EXAMPLE

Examples of the invention are given below by way of illustration and not by way of limitation.

(1) Synthesis of 2-Cyanoethyl-Containing Organoxysilane

Example 1-1

Synthesis of Compound (1-1)

(1-1)

A 100-mL three-neck flask equipped with a reflux condenser and stirrer was purged with nitrogen and charged with 179.1 g (1.00 mol) of 3-aminopropyltrimethoxysilane and 4.5 g (0.03 mol) of trifluoromethanesulfonic acid. To the flask at 110° C., 118.1 g (2.22 mol) of acrylonitrile was added dropwise over 4.5 hours. At the end of dropwise addition, the reaction solution was heated and stirred at 120° C. for 13 hours.

To the reaction solution, 5.9 g (0.03 mol) of 28 wt % sodium methoxide methanol solution was added for neutralization, whereupon 70.3 mg of succinic acid was added. The reaction solution was distilled, collecting 168.8 g of a fraction having a boiling point of 192-193° C./0.16 kPa.

On analysis by GC-MS and $^1$H-NMR spectroscopy, the liquid was identified to be Compound (1-1).

GC-MS (EI) m/z: 285 (M$^+$), 245

$^1$H-NMR (600 MHz, δ in CDCl$_3$):
0.60-0.67 (m, 2H), 1.51-1.59 (m, 2H), 2.46 (t, J=7.2 Hz, 4H), 2.51-2.55 (m, 2H), 2.85 (t, J=6.9 Hz, 4H), 3.57 (s, 9H) ppm.

Example 1-2

Synthesis of Compound (1-5)

(1-5)

A 100-mL three-neck flask equipped with a reflux condenser and stirrer was purged with nitrogen and charged with 47.0 g (0.20 mol) of 3-(butylamino)propyltrimethoxysilane and 334.5 mg (0.002 mol) of trifluoromethanesulfonic acid. To the flask at 115-125° C., 11.4 g (0.21 mol) of acrylonitrile was added dropwise over 2.5 hours. At the end of dropwise addition, the reaction solution was heated and stirred at 115° C. for 1.5 hours.

To the reaction solution, 460.6 g (0.002 mol) of 28 wt % sodium methoxide methanol solution was added for neutralization, whereupon 28.1 mg of succinic acid was added. The reaction solution was distilled, collecting 43.1 g of a fraction having a boiling point of 136-137° C./0.15 kPa.

On analysis by GC-MS and $^1$H-NMR spectroscopy, the liquid was identified to be Compound (1-5).

GC-MS (EI) m/z: 288 (M), 248

$^1$H-NMR (600 MHz, δ in CDCl$_3$):

0.59-0.65 (m, 2H), 0.90 (t, J=7.2 Hz, 3H), 1.27-1.34 (m, 2H), 1.37-1.43 (m, 2H), 1.49-1.56 (m, 2H), 2.39-2.45 (m, 6H), 2.77 (t, J=7.2 Hz, 2H), 3.56 (s, 9H) ppm.

Example 1-3

Synthesis of Compound (1-9)

A 100-mL three-neck flask equipped with a reflux condenser and stirrer was purged with nitrogen and charged with 50.0 g (0.25 mol) of 3-(methylamino)propyltrimethoxysilane and 350.1 mg (0.0023 mol) of trifluoromethanesulfonic acid. To the flask at 80-105° C., 17.8 g (0.33 mol) of acrylonitrile was added dropwise over 1.5 hours. At the end of dropwise addition, the reaction solution was heated and stirred at 95° C. for 1.5 hours.

To the reaction solution, 452.4 g (0.0023 mol) of 28 wt % sodium methoxide methanol solution was added for neutralization, whereupon 27.1 mg of succinic acid was added. The reaction solution was distilled, collecting 53.9 g of a fraction having a boiling point of 121° C./0.18 kPa.

On analysis by GC-MS and $^1$H-NMR spectroscopy, the liquid was identified to be Compound (1-9).

GC-MS (EI) m/z: 246 (M$^+$), 206

$^1$H-NMR (600 MHz, δ in CDCl$_3$):

0.60-0.67 (m, 2H), 1.52-1.59 (m, 2H), 2.25 (s, 3H), 2.36-2.40 (m, 2H), 2.45 (t, J=7.2 Hz, 2H), 2.70 (t, J=7.2 Hz, 2H), 3.56 (s, 9H) ppm Example 1-4

Synthesis of Compound (1-11)

A 100-mL three-neck flask equipped with a reflux condenser and stirrer was purged with nitrogen and charged with 29.1 g (0.10 mol) of 1-(3-triethoxysilylpropyl)piperazine. To the flask at 71-78° C., 5.8 g (0.11 mol) of acrylonitrile was added dropwise over 1.5 hours. At the end of dropwise addition, the reaction solution was heated and stirred at 75° C. for 2.0 hours.

The reaction solution was distilled, collecting 22.2 g of a fraction having a boiling point of 158-160° C./0.08 kPa.

On analysis by GC-MS and $^1$H-NMR spectroscopy, the liquid was identified to be Compound (1-11).

GC-MS (EI) m/z: 343 (M$^+$)

$^1$H-NMR (600 MHz, δ in CDCl$_3$):

0.56-0.62 (m, 2H), 1.20 (t, J=6.9 Hz, 9H), 1.54-1.61 (m, 2H), 2.30-2.35 (m, 2H), 2.47-2.51 (m, 2H), 3.79 (q, J=6.9 Hz, 6H) ppm (2) Synthesis of Silsesquioxane Example 2-1

Synthesis of Silsesquioxane from Compound (1-1)

A 100-mL four-neck round-bottom flask equipped with a stirrer, thermometer, reflux condenser and dropping funnel was purged with nitrogen, and nitrogen was passed to the top of the reflux condenser, which was open to the ambient air, for shutting off air and moisture. The flask was charged with 14.27 g (50 mmol) of Compound (1-1) and 5 g of acetone. With stirring, 2.70 g (150 mmol) of deionized water was added to the mixture, which was stirred at room temperature for 20 hours. The reaction mixture was analyzed by gel permeation chromatography (GPC), finding that Compound (1-1) vanished. The reaction mixture was concentrated under reduced pressure. The residue was heat dried in vacuum at 80° C., yielding a pale yellow oily matter.

Figure 1:
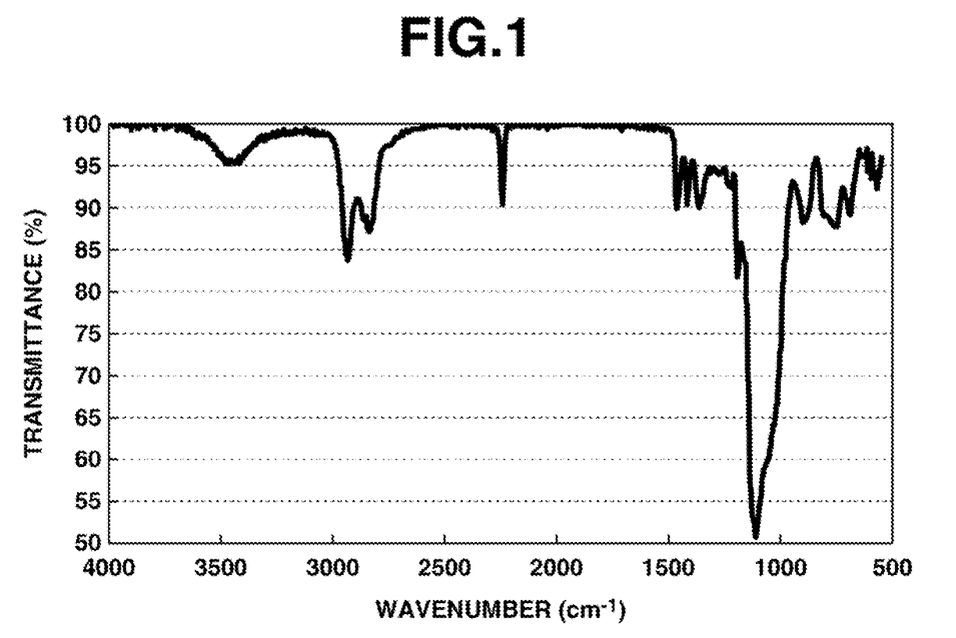
FIG. 1 is a diagram showing IR spectrum of a silsesquioxane in Example 2-1.

FIG. 1 shows an infrared absorption spectrum of the oily matter. As seen from FIG. 1, a stretching vibration peak of cyano group was observed at 2,247 cm$^{-1}$ and a stretching vibration peak of Si—O bond observed at 1,000-1,100 cm$^{-1}$. It was concluded that the desired silsesquioxane was obtained.

Example 2-2

Synthesis of Silsesquioxane from Compound (1-5)

A 100-mL four-neck round-bottom flask equipped with a stirrer, thermometer, reflux condenser and dropping funnel was purged with nitrogen, and nitrogen was passed to the top of the reflux condenser, which was open to the ambient air, for shutting off air and moisture. The flask was charged with 14.42 g (50 mmol) of Compound (1-5) and 5 g of acetone. With stirring, the mixture was temperature adjusted at 50° C. Then 2.70 g (150 mmol) of deionized water was added to the mixture, which was stirred at 50° C. for 10 hours. The reaction mixture was analyzed by GPC, finding that Compound (1-5) vanished. The reaction mixture was concentrated under reduced pressure. The residue was heat dried in vacuum at 80° C., yielding a pale yellow oily matter.

Figure 2:
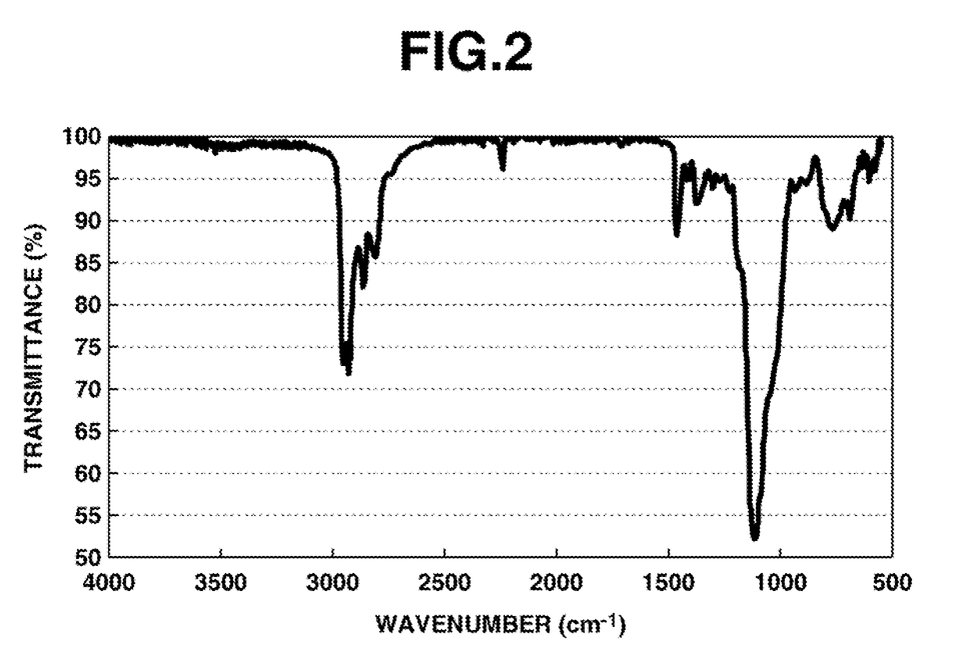
FIG. 2 is a diagram showing IR spectrum of a silsesquioxane in Example 2-2.

FIG. 2 shows an IR spectrum of the oily matter. As seen from FIG. 2, a stretching vibration peak of cyano group was observed at 2,247 cm$^{-1}$ and a stretching vibration peak of Si—O bond observed at 1,000-1,100 cm$^{-1}$. It was concluded that the desired silsesquioxane was obtained.

Example 2-3

Synthesis of Silsesquioxane from Compound (1-9)

A 100-mL four-neck round-bottom flask equipped with a stirrer, thermometer, reflux condenser and dropping funnel was purged with nitrogen, and nitrogen was passed to the top of the reflux condenser, which was open to the ambient air, for shutting off air and moisture. The flask was charged with 12.32 g (50 mmol) of Compound (1-9) and 5 g of acetone. With stirring, 2.70 g (150 mmol) of deionized water was added to the mixture, which was stirred at room temperature for 20 hours. The reaction mixture was analyzed by GPC, finding that Compound (1-9) vanished. The reaction mixture was concentrated under reduced pressure. The residue was heat dried in vacuum at 80° C., yielding a pale yellow oily matter.

Figure 3:
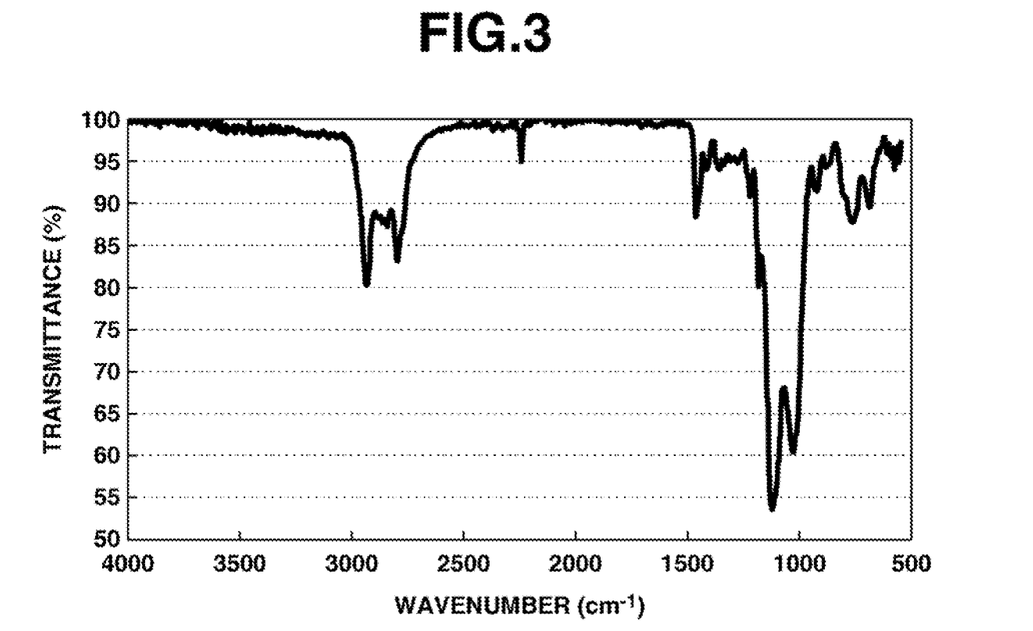
FIG. 3 is a diagram showing IR spectrum of a silsesquioxane in Example 2-3.

FIG. 3 shows an IR spectrum of the oily matter. As seen from FIG. 3, a stretching vibration peak of cyano group was observed at 2,247 cm$^{-1}$ and a stretching vibration peak of Si—O bond observed at 1,000-1,100 cm$^{-1}$. It was concluded that the desired silsesquioxane was obtained.

Example 2-4

Synthesis of Silsesquioxane from Compound (1-11)

A 100-mL four-neck round-bottom flask equipped with a stirrer, thermometer, reflux condenser and dropping funnel was purged with nitrogen, and nitrogen was passed to the top of the reflux condenser, which was open to the ambient air, for shutting off air and moisture. The flask was charged with 17.18 g (50 mmol) of Compound (1-11) and 5 g of acetone. With stirring, 2.70 g (150 mmol) of deionized water was added to the mixture, which was stirred at room temperature for 20 hours. The reaction mixture was analyzed by GPC, finding that Compound (1-11) vanished. The reaction mixture was concentrated under reduced pressure. The residue was heat dried in vacuum at 80° C., yielding a white solid.

Figure 4:
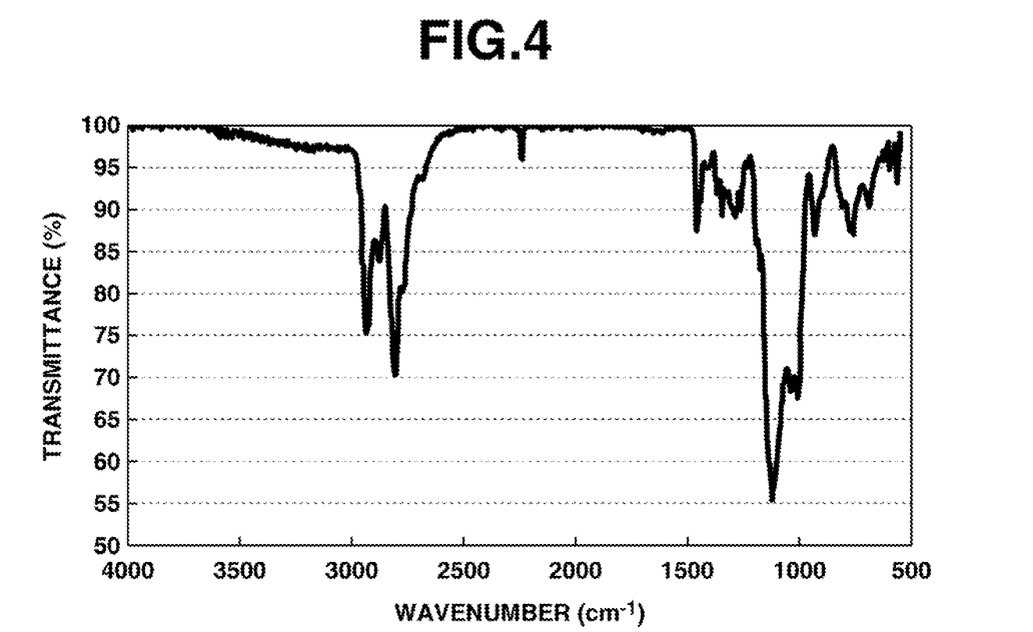
FIG. 4 is a diagram showing IR spectrum of a silsesquioxane in Example 2-4.

FIG. 4 shows an IR spectrum of the solid. As seen from FIG. 4, a stretching vibration peak of cyano group was observed at 2,247 cm$^{-1}$ and a stretching vibration peak of Si—O bond observed at 1,000-1,100 cm$^{-1}$. It was concluded that the desired silsesquioxane was obtained.

Example 2-5

Synthesis of Silsesquioxane from Compound (1-5) and Cyanoethyltriethoxysilane

A 100-mL four-neck round-bottom flask equipped with a stirrer, thermometer, reflux condenser and dropping funnel was purged with nitrogen, and nitrogen was passed to the top of the reflux condenser, which was open to the ambient air, for shutting off air and moisture. The flask was charged with 3.46 g (12 mmol) of Compound (1-5), 8.69 g (40 mmol) of cyanoethyltriethoxysilane, 0.26 g (2.6 mmol) of triethylamine, and 5.2 g of acetone. The mixture was temperature adjusted at 50° C. Then 2.81 g (156 mmol) of deionized water was added to the mixture, which was stirred at 50° C. for 10 hours. The reaction mixture was analyzed by GPC, finding that Compound (1-5) and cyanoethyltriethoxysilane vanished. The reaction mixture was concentrated under reduced pressure. The residue was heat dried in vacuum at 80° C., yielding a white solid.

Figure 5:
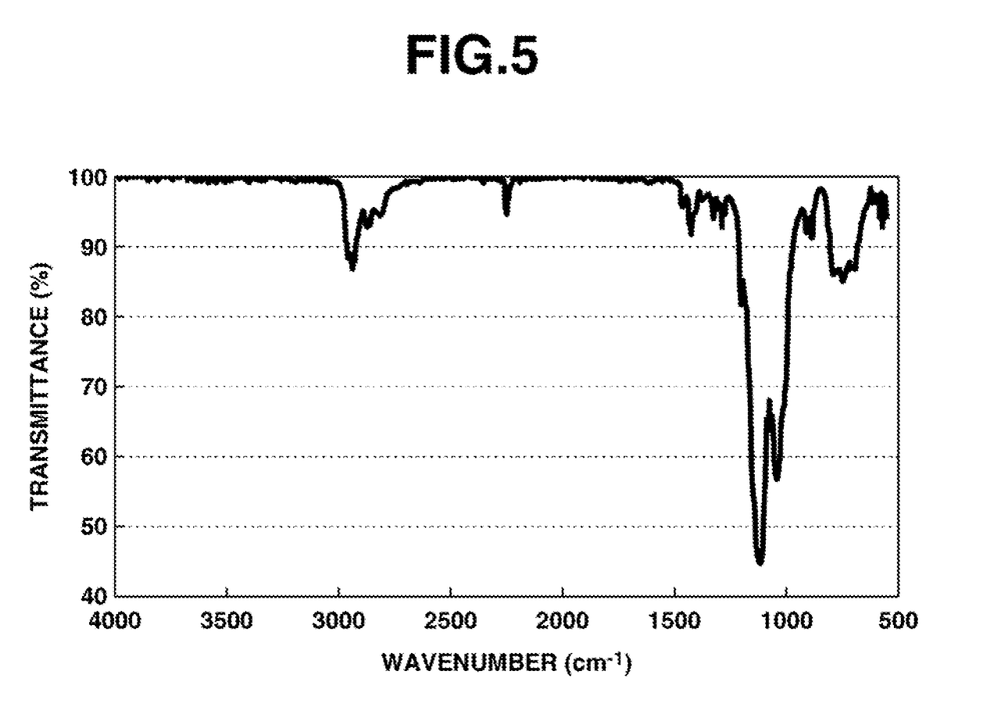
FIG. 5 is a diagram showing IR spectrum of a silsesquioxane in Example 2-5.

FIG. 5 shows an IR spectrum of the solid. As seen from FIG. 5, a stretching vibration peak of cyano group was observed at 2,249 cm$^{-1}$ and a stretching vibration peak of Si—O bond observed at 1,000-1,100 cm$^{-1}$. It was concluded that the desired silsesquioxane was obtained.

Japanese Patent Application No. 2016-173335 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A 2-cyanoethyl-containing organoxysilane compound having the general formula (1):

$$NC-CH_2-CH_2-X-Si(OR^1)_3 \quad (1)$$

wherein
each $R^1$ is independently a $C_1$-$C_{20}$ straight chain, branched, or cyclic monovalent hydrocarbon group, and X is a $C_2$-$C_{20}$ straight chain, branched, or cyclic divalent hydrocarbon group which contains a methylene and/or methine moiety, at least one of the methylene and methine moieties being substituted by a divalent heteroatom linking moiety NR, wherein R is a $C_1$-$C_{20}$ straight chain alkyl group, a $C_3$-$C_{20}$ branched alkyl group, a $C_3$-$C_{20}$ cyclic alkyl group, a $C_6$-$C_{20}$ aryl group, or a $C_7$-$C_{20}$ aralkyl group, with the proviso that the heteroatom linking moieties do not adjoin each other, the heteroatom linking moiety does not adjoin a silicon atom, and the NC—CH$_2$—CH$_2$— linkage is bonded to the heteroatom linking moiety included in X.

2. The compound of claim 1 wherein R is a $C_1$-$C_5$ straight chain alkyl group, $C_3$-$C_6$ branched alkyl group, or $C_3$-$C_6$ cyclic alkyl group.

* * * * *